United States Patent
Bott et al.

(10) Patent No.: US 6,812,019 B1
(45) Date of Patent: Nov. 2, 2004

(54) PROCESS FOR THE RECOMBINANT PRODUCTION OF HOLO-CITRATE LYASE

(75) Inventors: Michael Bott, Juelich (DE); Peter Dimroth, Kuesnacht (CH); Karin Schneider, Zurich (CH)

(73) Assignee: Roche Diagnostics GmbH (DE)

( * ) Notice: Subject to any disclaimer, the term of this patent is extended or adjusted under 35 U.S.C. 154(b) by 0 days.

(21) Appl. No.: 09/672,265

(22) Filed: Sep. 28, 2000

(30) Foreign Application Priority Data

Sep. 30, 1999 (EP) .............................. 99119404

(51) Int. Cl.[7] .................................. C12N 9/88
(52) U.S. Cl. ..................................... 435/232
(58) Field of Search ......................... 435/232

(56) References Cited

FOREIGN PATENT DOCUMENTS

| DE | DD273073 A1 | 11/1989 |
|---|---|---|
| GB | 2185317 A | 7/1987 |

OTHER PUBLICATIONS

Bott, M., et al. (1995) Mol. Microbiol. 18(3), 533–546.*
Blattner, F.R., et al. (1997) Science 277, 1453–1474.*
Oshima, et al. (1999) Accession No. D90702.*

Sadjia Bekal et al. "Purification of Leuconostoc mesenteroides Citrate Lyase and Cloning and Characterization of the citCDEFG Gene Cluster" Journal of Bacteriology, Feb. 1998, p. 647–654, vol. 180. No. 3.

Michael Bott et al. "Klebsiella pneumoniae genes for citrate lyase and citrate lyase ligese: localization, sequencing, and expression" Molecular Microbiology (1994) 14 (2). P.347–356.

* cited by examiner

*Primary Examiner*—Charles L. Patterson, Jr.
(74) *Attorney, Agent, or Firm*—Marilyn L. Amick; Roche Diagnostics Operations, Inc.

(57) ABSTRACT

Process for the production of a protein with citrate lyase activity by expressing a suitable plasmid in a host organism and isolating the protein in an active form, wherein the plasmid contains the information from a gene cluster composed of at least six genes and an inducible promoter. Furthermore the invention concerns the use of the recombinant enzyme and a corresponding test kit for the determination of citric acid.

5 Claims, 2 Drawing Sheets

```
                         SEQUENCE LISTING

<160> NUMBER OF SEQ ID NOS: 7

<210> SEQ ID NO 1
<211> LENGTH: 36
<212> TYPE: DNA
<213> ORGANISM: Escherichia coli

<400> SEQUENCE: 1
ccctctagag aacaacattc gttgcaaatc gataac                             36

<210> SEQ ID NO 2
<211> LENGTH: 38
<212> TYPE: DNA
<213> ORGANISM: Escherichia coli

<400> SEQUENCE: 2
ccgcgaattc ttagttccac atggcgagaa tcggccag                           38

<210> SEQ ID NO 3
<211> LENGTH: 5484
<212> TYPE: DNA
<213> ORGANISM: Escherichia coli

<400> SEQUENCE: 3
gaacaacatt cgttgcaaat cgataacaac atgcaccttc aggatactat ttattatgtt    60
cggcaatgat attttcaccc gcgtaaaacg ttcagaaaat aaaaaaatgg cggaaatcgc   120
ccaattcctg catgaaaatg atttgagcgt tgacaccaca gtcgaagtat ttattaccgt   180
aacccgcgat gaaaagctta tcgcgtgcgg tggaattgcc ggaaatatta ttaaatgcgt   240
tgctatcagt gaatccgtcc gcggtgaagg actggcgctg acattagcca ctgaattgat   300
aaacctcgcc tatgagcggc acagcacgca tctgtttatt tataccaaaa ccgaatacga   360
ggcgctgttc cgccagtgcg gttttttccac gctgaccagc gtacccggcg tgatggtgct   420
gatggaaaac agcgccacgc gactgaaacg ctatgccgaa tcgctgaaaa aatttcgtca   480
tccagggaac aagattggct gcattgtgat gaacgccaat ccctttacga atggtcaccg   540
ttatctgatt caacaggctg cggcacagtg cgactggttg catctgtttt tagtcaaaga   600
agattcttca cgcttcccct atgaagaccg gctggatttg gtgttaaaag gcaccgccga   660
tattccacgc ctgactgtgc atcgtggctc cgaatacatc atctcccgcg ctacgttccc   720
```

-continued

```
ttgctacttc attaaagaac agagcgtcat taaccattgt tacaccgaaa ttgatctgaa        780
gattttccgt cagtacctcg ctcccgcgct gggtgtaact caccgctttg tcggtactga        840
acccttttgt cgcgttaccg cccagtacaa ccaggatatg cgctactggc tggaaacgcc        900
gactatctcc gcaccgccca tcgaactggt tgaaattgag cggctgcgtt accaggagat        960
gccgatatcc gcttcccggg tacgtcaact gctggcgaaa aacgatctca cggctatcgc       1020
gccgctggtc cctgcagtca cgctgcatta tttgcagaac ctgcttgagc actcccgcca       1080
ggacgcggca gctcgtcaaa agaccccgc atgagaaaca ggtgaaaaat gaaataaac        1140 cagcccgccg ttgcaggcac ccttgagtct ggggatgtga tgatacgcat cgccccactc       1200
gatacgcagg atatcgacct gcaaatcaat agcagcgttg agaaacagtt tggcgatgca       1260
attcgcacca ccattctgga cgttctcgcc cgctacaacg tgcgcggcgt acagctgaat       1320
gtcgatgaca aaggcgcact ggactgcatt ttacgtgcac gactggaagc cctgctggca       1380
cgcgccagcg gtatcccggc tctgccatgg gaggattgcc aatgatttcc gcttcgctgc       1440
aacaacgtaa aactcgcacc cgccgcagca tgttgtttgt gcctggtgcc aatgccgcga       1500
tggtcagcaa ctccttcatc tacccggctg atgcccgat gtttgacctc gaagactccg        1560
tagcattgcg tgaaaaagac accgcccgcc gcatggttta ccacgcgctg caacatccgc       1620
tgtatcgcga tattgaaacc attgtgcgtg tcaacgcgct ggattccgaa tggggtgtta       1680
acgacctgga agccgtcgtt cgcggtggtg cggacgttgt gcgtctgccg aaaaccgata       1740
ccgctcagga tgttctggat attgaaaaag agatcctgcg tatcgaaaaa gcctgtggtc       1800
gtgaacccgg cagcaccggc ctgctggcgg cgattgaatc tccgctgggg attacccgcg       1860
cagtggaaat cgctcacgct tccgagcgtt tgatcggtat cgccctcggt gcagaagact       1920
atgtgcgcaa cctgcgtaca gaacgctccc cggaaggaac tgaactgctg ttcgcacgct       1980
gttccatttt gcaggccgcg cgctctgcgg gtattcaggc gttcgatacc gtctattccg       2040
acgctaacaa cgaagccgga tttctgcaag aagccgccca catcaaacag ctgggctttg       2100
acggcaaatc gctgatcaac ccgcgtcaga ttgatctgct gcacaacctc tacgcaccga       2160
cccagaaaga agtggatcac gcccgccgcg tcgtagaagc cgctgaagcc gccgctcgcg       2220
aaggcctcgg cgtggtttcc ctgaacggca agatggtgga cggtccggtt atcgatcgcg       2280
cccgtctggt gctctcccgt gcagaacttt ccggcatccg cgaagaataa ggcaatcaaa       2340
atgacgcaga aaattgaaca atctcaacga caagaacggg tagcggcctg gaatcgtcgc       2400
gctgaatgcg atcttgccgc tttccagaac tcgccaaagc aaacctacca ggctgaaaaa       2460
gcgcgcgatc gcaaactgtg cgccaacctg gaagaagcga ttcgtcgctc tggtttacag       2520
gacggcatga cggtttcctt ccatcacgct ttccgtggcg gtgacctgac cgtcaatatg       2580
gtgatggacg tcatcgcgaa gatgggcttt aaaaacctga ccctggcgtc cagctccctg       2640
agtgattgcc atgcgccgct ggtagaacac attcgccagg gcgtggttac ccgcatttat       2700
acctccggcc tgcgtggtcc actggcggaa gagatctccc gtggtctgct ggcagaaccg       2760
gtgcagatcc actctcacgg cggtcgtgtg catctggtac agagcggcga actgaatatc       2820
gacgtggctt tcctcggcgt cccgtcctgt gatgaattcg gtaatgccaa cggctacacc       2880
ggtaaagcct gctgcggctc cctcggctat gcaatagttg atgccgacaa cgcaaaacag       2940
gtcgtgatgc ttaccgaaga actgctgcct tatccgcata atccggcaag cattgagcaa       3000
gatcaggttg atttgatcgt caaagttgac cgcgttggcg atgctgcaaa aatcggcgct       3060
```

-continued

```
ggcgcgaccc gtatgaccac taacccgcgc gaactgctta ttgcccgtag cgctgcggat    3120
gtgattgtca actctggcta cttcaaagaa ggtttctcca tgcaaaccgg caccggcggc    3180
gcatcgctgg cggtaacccg tttcctggaa gacaaaatgc gtagccgcga tattcgcgcc    3240
gacttcgccc ttggcggtat taccgcgacg atggttgacc tgcacgaaaa aggtctgatc    3300
cgcaaactgc tggatgtgca gagctttgac agccatgctg cgcaatcgct ggcccgtaac    3360
cccaatcaca tcgaaatcag cgccaaccag tacgctaact ggggttcgaa aggcgcatcg    3420
gttgatcgtc tcgacgtggt ggtactgagc gcgctggaaa ttgacaccca gttcaacgtt    3480
aacgtgctga ccggctctga cggcgtactg cgtggtgctt ccggtggtca ctgcgatacc    3540
gcgattgcct ctgcgctttc catcatcgtc gcgccgctgg tacgcggtcg tattccgact    3600
ctggtggata acgtactgac ctgcatcacc ccaggctcca gtgtcgatat tctggtcaca    3660
gaccacggta tcgcagttaa cccggcacgt ccggaactgg cagaacgtct gcaggaagcg    3720
ggcattaaag tggtttccat tgagtggctg cgcgaacgtg cgcgtctgct gaccggtgaa    3780
ccacagccga ttgaattcac agaccgcgtc gttgccgttg tgcgttaccg cgatggctcg    3840
gtgatcgatg ttgtgcatca ggtgaaggaa taagccatgc acctgcttcc tgaactcgcc    3900
agccaccatg cggtatcaat tcccgagctg ctcgtcagcc gggatgaaag gcaagcacgg    3960
caacacgtct ggctcaagcg ccatcctgtt ccactggtct cctttaccgt ggttgcgcct    4020
gggccgatta agacagcga ggtcacacgc gaattttta atcatggcgt gacagccttg    4080
cgtgccttag ccgcaaaaca gggctggcaa attcaggagc aggctgcact ggtttccgcc    4140
agcgggccgg agggcatgtt gagcattgcc gccccggctc gcgacctcaa gctcgccacc    4200
attgagcttg aacatagtca tcctctcggg cggttatggg atatcgatgt cctgacgccc    4260
gaaggcgaaa ttctctcccg ccgcgactat tcactgccgc ctcgccgctg cctgttgtgc    4320
gaacaaagcg cagccgtctg cgcgcgtgga aaaacccatc aactgaccga tttactcaac    4380
cgcatggagg cactgctgaa cgatgtcgat gcctgcaacg tcaactaaaa ccacaaagct    4440
tgcgacgtca ttaatcgatg agtacgcccct gctgggctgg cgcgccatgc tgactgaagt    4500
caatctgtca ccgaaaccag gcctcgtgga tcgcattaac tgcggtgcgc acaaagatat    4560
ggcgctggaa gatttccacc gcagcgcgct ggcgattcag ggctggctac cccgtttcat    4620
tgaatttggt gcctgtagtg cggaaatggc accagaagcg gtactccacg gattacgccc    4680
aattggtatg gcttgcgaag gtgatatgtt ccgcgccact gcgggcgtaa acacgcataa    4740
aggcagcatt ttttctttag ggctgctatg tgcggcaatt ggccgtttgc ttcaactcaa    4800
ccaaccggta acgccaacaa ccgtttgttc tacggcggca agtttctgcc gtggcctgac    4860
cgatcgcgaa ctgcgtacca ataattcaca actgacggca ggtcaacggt tgtaccaaca    4920
gcttggcctt accggcgcac gcggtgaagc cgaagcgggt tatccactgg tgatcaatca    4980
cgccttgccg cattacctca ctctgctgga tcaggggtta gatcctgaac tggcattgct    5040
cgataccttg ctcctactga tggcgatcaa cggcgatacc aacgttgcat cgcgcggtgg    5100 cgagggggggc ctgcgctggc tacagcgcga ggcgcaaaca ttattgcaaa aaggggggcat    5160 tcgaaccccc gccgatctcg attatctccg gcagttcgac agggagtgta tcgaacgaaa    5220
tctcagtcca ggcggcagtg ctgacctact gatcctacc tggttttttag cacagattta    5280 attatttaag cacttgataa atttggaaat attaattttc ggagaacccg tatgtcttta    5340
gcaaaagata atatatggaa actattggcc ccactggtgg tgatgggtgt catgtttctt    5400
atccctgtcc ccgacggtat gccgccgcag gcatggcatt acttcgctgt gtttgtggca    5460
```

```
atgattgtcg gcatgatcct cgag                                          5484

<210> SEQ ID NO 4
<211> LENGTH: 33
<212> TYPE: DNA
<213> ORGANISM: Escherichia coli

<400> SEQUENCE: 4
aaatttcata tgcacctgct tcctgaactc gcc                                  33

<210> SEQ ID NO 5
<211> LENGTH: 36
<212> TYPE: DNA
<213> ORGANISM: Escherichia coli

<400> SEQUENCE: 5
gggcccctcg agttagttga cgttgcaggc atcgac                               36

<210> SEQ ID NO 6
<211> LENGTH: 552
<212> TYPE: DNA
<213> ORGANISM: Escherichia coli

<400> SEQUENCE: 6
atgcacctgc ttcctgaact cgccagccac catgcggtat caattcccga gctgctcgtc     60
agccgggatg aaaggcaagc acggcaacac gtctggctca agcgccatcc tgttccactg    120
gtctccttta ccgtggttgc gcctgggccg attaaagaca gcgaggtcac acgccgaatt    180
tttaatcatg gcgtgacagc cttgcgtgcc ttagccgcaa acagggctg gcaaattcag     240 gagcaggctg cactggtttc cgccagcggg ccggagggca tgttgagcat tgccgccccg    300
gctcgcgacc tcaagctcgc caccattgag cttgaacata gtcatcctct cgggcggtta    360
tgggatatcg atgtcctgac gcccgaaggc gaaattctct cccgccgcga ctattcactg    420
ccgcctcgcc gctgcctgtt gtgcgaacaa agcgcagccg tctgcgcgcg tggaaaaacc    480
catcaactga ccgatttact caaccgcatg gaggcactgc tgaacgatgt cgatgcctgc    540
aacgtcaact aa                                                        552

<210> SEQ ID NO 7
<211> LENGTH: 5593
<212> TYPE: DNA
<213> ORGANISM: Klebsiella pneumoniae

<400> SEQUENCE: 7
ttaattaaca acataaaaac cataaagcca attaagccac gagaaaaact gtgacttaaa     60
tacaagaatc catagccgaa cgctggcgaa atacagttcg ttttgaaatg acgaagcgct    120
aaaaaatgac actgatatta aaacgcgttc agctattaaa agataaaccg cggcgagagg    180
cgatcgatcg gtttctccgc cagcatcaac tgtcgttaga ggccgactgc gaaatggcga    240
ttatcgccga gtatcagcag cggctggtcg gctgcggtgc tatcgccggc aatgtgctga    300
aatgcatcgc catcgatccc tcgctgcagg ggagggggct gagccttaaa ttactgaccg    360
agctcctgac gctggcctat gagctggggc gcagcgaact gttttttgttc actaaacctt    420 gcaatgccgc gttattttcc ggcgccggct tctggccgat agcccaggcg ggcgaccgcg    480
ccgtgctaat ggaaaatagc cgcgaacggc tgactcgtta ctgtcgacag ctggcgatgt    540
accgtcagcc gggaagaaaa atcggcgcta tcgtgatgaa tgctaatcca ttcaccctcg    600
```

```
gccaccgctg gttggtagaa caggcggcca gccagtgcga ctggctgcat ctgtttgtgg      660
tcaaagaaga tgcgtcctgc ttttcctatc acgatcgctt caagctcatt gaacagggga      720
ttaccggcat cgataaggtg acgctgcatc ccggttcggc gtatctgatc tcgcgggcga      780
cgttccccgg ctatttcctg aaagagcagg gggtggttga tgactgccac agccagattg      840
acctgcagct cttccgcgag cgcctggccc cggcgctgca gattacccat cgctttgtcg      900
gcaccgagcc gctgtgtccc ctgacccgta attacaacca gcgcatgaag tcactactgg      960
aagcgccagg cgacgcgccg cccattgaag tagttgagct tgcgcgaatc gaaaaaaatg     1020
gtggacccgt gtcggcctcc cgagtgcgcg aactctatcg acagcgcaac tggcaggcgg     1080
tcgcggcgct ggtaccgccg ggaaccctct cttttctgat gcaactggcg aaagcgaac      1140 atcaaaccgc ctgatttata cgccctaact aaggattttc ccctatggaa atgaagattg     1200
acgccctggc cggcacgctg gagtccagcg atgtgatggt caggattgga cccgcggcgc     1260
agccgggcat tcagctggaa atcgacagca ttgtgaaaca acagtttggc gctgcgattg     1320
agcaggtagt gagagaaacg ctggctcagc ttggcgtgaa acaggccaac gtggtggtcg     1380
atgataaagg cgcgctggaa tgtgttttgc gagctcgcgt acaggccgcg gcgctgcgcg     1440
cggcgcaaca gacccaatta caatggagcc agctatgaaa ccacgtcgca gtatgttgtt     1500
catccctggc gccaatgccg ccatgttaag cacgtcattc gtctacggcg ctgatgctgt     1560
gatgttcgac ctggaagatg ccgtttcgct gcgcgagaaa gataccgctc gtctgctggt     1620
gtatcaggcg ctgcagcatc cactgtatca ggatatcgaa accgtggtgc gtattaaccc     1680
gctaaatacc ccgtttggtc tggccgatct ggaagccgtg gttcgtgcgg cgtggatat      1740 ggtgcgtctg ccgaaaaccg acagcaaaga agatatccat gagctggaag cgcatgttga     1800
gcggattgaa cgcgagtgcg gccgggaagt gggcagcacc aagttaatgg cggcgatcga     1860
gtcggcgctg ggcgtggtga acgcggtgga aatcgcccgc gccagcccgc gtctggcggc     1920
gatcgcgctg gcggccttcg attacgtgat ggatatgggc acctcccgcg gcgacggtac     1980
tgaactgttc tacgcccgct gcgctgtact gcatgccgcc cgcgttgccg gcatcgccgc     2040
ctatgacgtg gtgtggtcgg atatcaataa tgaagagggc ttcctggcgg aagcgaatct     2100
ggccaaaaac ctcggctta  acggcaaatc gttggttaac ccacgacaaa ttgaactcct     2160
gcatcaggtc tatgccccga cgcgcaaaga ggtcgatcac gcgctggaag tgattgccgc     2220 ggcgaagaa  gccgaaacgc gaggtctggg tgtggtatcg ctgaacggca agatgatcga     2280
tggaccgatt atcgaccatg ctcgcaaagt ggtggcgctc tcggcttccg gtattcgtga     2340
ttaaggggaa taagatgaaa gagacagtag caatgcttaa tcagcagtac gtgatgccga     2400
atggactgac accttatgcc ggcgtaacgg cgaaaagtcc ctggctggcg agtgagagcg     2460
aaaagcgcca gcgcaaaatc tgcgattcgc tggaacggc  aatccgtcgc tccggcctgc     2520
aaaacggcat gaccatctcg tttcaccacg cgtttcgcgg cggtgacaaa gtcgtcaata     2580
tggtagtggc gaagctggcg gaaatggggtt ttcgcgatct caccctggcg tccagttcgc     2640
tgatcgacgc ccactggccg ctgatcgagc atattaaaaa tggcgtgatc cgccagatct     2700
acacctccgg cctgcgcggc aagttgggcg aggagatctc cgccggttta atggaaaacc     2760
cggtgcagat ccactcccac ggcggtcgcg tacagctgat tcaaagcggc gagctgtcga     2820
ttgatgtcgc gttttctcggc gttccttgct gcgatgagtt tggcaacgcc aacggctta      2880 gcggtaaatc acgctgcggt tctctgggct acgcgcgcgt cgatgccgag cacgctaaat     2940
gcgtggtgct gctcaccgaa gagtgggtgg attatcctaa ctatccggcc agtattgccc     3000
```

-continued

```
aggatcaggt ggatctgata gtccaggtag atgaagtcgg cgatccgcaa aaaattaccg    3060
cgggtgccat ccgtctgacc agcaacccgc gcgagctgct gatcgcccgc caggcggcga    3120
aagtcgttga gcactccggt tactttaaag agggtttctc gctgcagacc ggtaccggcg    3180
gcgcctcgct ggcagtaact cgcttccttg aagataaaat gcgccgtaac ggcattaccg    3240
ccagcttcgg cctcggcggt atcaccggga cgatggtcga tttgcacgaa aaagggttga    3300
tcaaaacgct gctcgatacc cagtccttcg atggtgacgc ggcgcgttcg ctggcgcaga    3360
acccgaacca tgtcgagatc tccaccaatc agtatgccag cccgggctcc aaaggcgcct    3420
cctgcgagcg cttaaacgtg gtgatgctca gcgcgctgga aattgatatc gactttaacg    3480
ttaacgtgat gaccggttct aacggtgtgc tgcgcggggc gtccggtggc catagcgata    3540
ccgccgccgg tgcggatttg accattatta ccgcgccgtt agttcgcggc cgtattccct    3600
gcgtcgtgga aaaggtgctg acccgcgtca cgccgggggc cagcgtggat gtgctggtca    3660
ctgaccacgg cattgcggtc aacccggcac gtcaggacct gatcgacaat ttgcgcagcg    3720
caggcattcc gctgatgacc attgaggaac tgcagcagcg tgctgagctg ttgactggca    3780
agccgcagcc gatcgaattc accgatcggg tggtggcggt ggtgcgctat cgcgacggtt    3840
cggtcatcga tgtgattcgt caggtgaaaa acagcgacta aacgcagagg ggaaaggcca    3900
tgagcgacgt gttaattaat cctgcgcgtg tgcggcgcgt gaagccactg agtgccgaag    3960
aggtggtcag cgcggtagag cgcgcgctgt tgaccgaagt tcgcctgacc ccaaagcccg    4020
ggttggtgga tattcgtaac gctggcgcgc actgggatat ggatctggcc tcgtttgagg    4080
ccagcaccgc ggtggtggct ccgtggatgg agaaattttt catcatgggc cacgatactg    4140
cggcggtcgc gccggagcag gtattgatga tgctgcgccc ggtagggatg gcctgtgaga    4200
acgatatgct ggaggccacc ggcggggtga atacccatcg cggggcgatc ttcgcttttg    4260
gcctgctcag cgcggcggcg ggcaggctgg tgtcgaaagg tgagccgata gagcagcacc    4320
ggctttgcga ccaggtggcg cgcttctgtc gcggcatggt tatgcaggag ttgtcttctg    4380
ctggcgggga acggctcagt aaaggcgagg ctcattttct acgctatggt ctctccgggg    4440
cccgcggcga ggcggagagc ggtttcctga cggtgcgtac ccaggccatg ccagtcttta    4500
cccgcatgat ggaagagacc ggcgacagta atctggcgct actgcaaacc ctgctgcatc    4560
tgatggcgtg gaatgatgac accaacctgg tctcgcgcgg cgggcttgcc gggctgaact    4620
ttgtccagca ggaggcgcag cgactgctgt ggcaggcgg cgtgctggcg gacggcgggc    4680
tggaggcgct gcgacagttt gacgatgagc tgattgcccg ccatctcagc cctggcggca    4740
gcgccgatct gttggcggtg acctggtttt tatccgcgtt tcccgccggc gcgcttttcc    4800
cgctgtaacc cactgcaata ccgccttcgc ccgcactgta cgggcgaggg cgccatcatt    4860
agccttcccg gttgtcatcc ggtaaacacg gaatcgcggc acaatcgtat agttttttact    4920
gatatcgtcc gccgtttgtc ataaatttct aattatcggc gttttttgagt agcggcccgc    4980
tgacgggctg gttactctga aaacaattta cgtaatgtta acaaaagaga atagctatgc    5040
atgatgcaca aatccgcgtg ccatcgccg gcgcgggcgg ccggatggga cgccagttaa    5100
ttcaggctgc attgcagatg gaaggcgtgg cgctgggcgc ggcgctggag cgcgaagggt    5160
caagcctggt gggcagcgac gccggcgagc tggcgggcgc cggcaaagcg ggcgtcgcgg    5220
tgcagagcag cctggcggcg gtaaaagatg atttcgacgt gttgatcgat tttacccgcc    5280
cggaaggcac gctgaaccat ctggcgtttt gccgcgagca cggcaaaggg atggtcatcg    5340
```

| | | | | | |
|---|---|---|---|---|---|
| gcaccaccgg | ttttgacgac | gctggcaaac | aggcgattcg | cgatgccgcg | caggacattg | 5400 |
| ccattgtctt | cgccgctaac | tttagcgttg | gcgtcaatgt | cctgttgaag | ctgctggaga | 5460 |
| aggcggcgaa | ggtgatgggc | gactataccg | acatcgaaat | tatcgaagcg | caccaccggc | 5520 |
| ataaagtgga | tgcgccgtca | ggcaccgcgc | tggcgatggg | cgaagcgatc | gccgggcat | 5580 |
| tgaacaaaga | tct | | | | | 5593 |

PROCESS FOR THE RECOMBINANT PRODUCTION OF HOLO-CITRATE LYASE

The enzyme citrate lyase (EC4.1.3.6) is regarded as a key enzyme of anaerobic citrate degradation and can accordingly be isolated from a number of different prokaryotic cells. The enzyme catalyses the cleavage of citrate into acetate and oxaloacetate. Furthermore it is known that the enzyme complex of the citrate lyase enzyme that has been best examined to date from *Klebsiella pneumoniae* (formally: Klebsiella aerogenes) is composed of six copies of each of three different subunits and namely an α, β and γ subunit, of a molecular weight of about 550,000 Dalton. In addition it is known that the catalytically active center is located in the α and β subunit, whereas the γ subunit has the binding site for the prosthetic group 2'-(5"phosphoribosyl)-3'-dephospho CoA. This prosthetic group is bound to the serine residue 14 via a phosphodiester bond.

The citrate lyase enzyme is required in high purity for most applications which are primarily for clinical chemistry and food analysis. Hence the aim is to over-produce the enzyme in an active form in certain host cells by recombinant methods and to isolate it from these cells. Such a process has not yet been described or made known in other ways. Hence citrate lyase is nowadays usually isolated from *Klebsiella pneumoniae* cells which had been cultured under anaerobic conditions using citrate as the only carbon and energy source. The citrate lyase genes from *Klebsiella pneumoniae* have been cloned and sequenced (M. Bott and P. Dimroth, Mol. Microbiol. Vol. 14, 347–356 (1994)). These genes are part of the citC operon which is composed of the five genes citCDEFG. The citC gene codes for citrate lyase ligase which catalyses the formation of an acetyl thioester. The genes citD, citE and citF code for the gamma, beta and alpha subunit of citrate lyase. The protein coded by citG is involved in the biosynthesis of the prosthetic group. Furthermore it is known that the citC operon is induced in the absence of oxygen and in the presence of citrate and $Na^+$ ions; moreover the expression is strongly dependent on the citA/citB regulation system (M. Bott et al., Mol. Microbiol. Vol. 18, 533–546 (1995); M. Meyer et al., J. Mol. Biol. Vol. 269, 719–731 (1997)).

Expression of the genes coding for citrate lyase from *Klebsiella pneumoniae* which would preferably be carried out in prokaryotic cells such as *E. coli* for practical reasons, results in an inactive but nevertheless soluble form of the enzyme (M. Bott and P. Dimroth, Mol. Microbiol. Vol. 14, 347–356 (1994)). The recombinant apo-citrate lyase enzyme can be activated to form the holo-enzyme by subsequent addition of acetyl coenzyme A which is known as a substituent for the acetyl thioester of the native prosthetic group 2'-(5"-phosphoribosyl)-3'-dephospho CoA. However, such an additional activation measure is complicated and laborious. Moreover the necessity to add acetyl CoA is unsuitable for the commercial distribution of citrate lyase or the apo form since the substance decomposes when stored for long periods at 4° C.

Hence the object of the invention is to provide a recombinant, soluble and at the same time active holo-citrate lyase which eliminates the disadvantages of the known methods.

The object is achieved by a process for the production of a protein with citrate lyase activity by expressing a suitable plasmid in a host organisms whereby the plasmid contains the information of a gene cluster composed of at least six genes and an inducible promoter. The genes comprising the gene cluster code for certain subunits of the protein with citrate lyase activity and/or for a component which participates in the biosynthesis of the complete enzyme. In particular a suitable plasmid contains the genes citC, citD, citE, citF, citG and a DNA fragment that can for example be obtained from *E. coli* which is located between the genes citF and citG on the *E. coli* citrate lyase gene cluster. The genes citD, citE and citF code for the corresponding γ, β and α subunits of the enzyme and have molecular weights of about 11,000 Dalton, 32,000 Dalton and 55,000 Dalton. According to the invention it is preferred that one of the genes represents a DNA fragment which codes for a protein containing the motif G(A)-R-L-X-D-L(I)-D-V. A corresponding DNA fragment is particularly preferred which codes for a protein with a molecular weight of about 20,000 Dalton.

In addition it has proven to be advantageous when one gene and optionally a further gene fused to the first gene of the genes comprising the gene cluster is derived from a different organism than the other genes. In particular it has proven to be advantageous when the DNA fragment citX or genes homologous to citX located between citF and citG on the *E. coli* citrate lyase gene cluster are derived from *E. coli*, *Klebsiella pneumoniae*, *Haemophilus influenzae* or *Leuconostoc mesenteroides* and when one or several of the other genes are derived from the microorganism that is specific for the isolated protein having citrate lyase activity which is for example *Klebsiella pneumoniae*. In *Haemophilus influenza*, *Leuconostoc mesenteroides* (S. Bekal et al., J. Bacteriol. Vol. 180, 647–654 (1998)) and *Leuconostoc paramesenteroides* (M. Martin et al., FEMS Microbiol. Lett. Vol. 174, 231–238 (1999)) the genes citX and citG occur in a fused form. Thus corresponding fusion genes contain the information of two genes. The resulting proteins have a molecular weight of about 52,000 Dalton, have the activities of *E. coli* CitX and CitG and are thus bifunctional. In the absence of the citX gene or of a gene homologous to citG or of a corresponding citX fusion gene, only the low-molecular apo form (MW 12,000 Dalton, SDS-PAGE) but not the holo form of citrate lyase (MW 14,500 Dalton, SDS-PAGE) could be detected after expression.

According to the invention prokaryotes as well as eukaryotes have proven to be suitable as the host organism. The fact that a soluble active citrate lyase can now be produced in prokaryotes such as e.g. *E. coli* in a simple manner and in adequate yields without additional activation measures is a major advantage.

Hence it was possible to show that by cloning the entire *E. coli* citCDEFXG gene cluster under the control of an inducible promoter such as e.g. the lac, lac UV5, T5, tac or T7 promoter, an active enzyme can be expressed having citrate lyase activity even under non-oxygen limiting conditions. Cell extracts containing appropriate expression plasmids result in citrate lyase activities of about 4 to 5 U/mg protein in the cell-free extract whereas cells without recombinant citrate lyase have no citrate lyase activity when grown aerobically.

In addition the invention concerns the simultaneous expression of the citCDEFG gene cluster from *Klebsiella pneumoniae* and of the citX gene obtainable from *E. coli* by which means it is possible to obtain a corresponding citrate lyase in an active form even in prokaryotes and in particular in *E. coli*.

By this means it was possible to achieve an activity of about 8 U/mg total protein in a cell-free extract under aerobic growth conditions.

The holo-enzyme is purified by methods known to a person skilled in the art. About 100 to 120 μg soluble protein with citrate lyase activity can be obtained from about 1 g of cells (wet weight) using the process according to the invention. The protein determination was carried out according to P. K. Smith et al., Anal. Biochem. Vol. 150, 76–85 (1985) using ovalbumin as a standard. The specific activity of the citrate lyase is ca. 70 U/ml protein (M. Single and P. A. Srere, J. Biol. Chem. Vol. 251 (10), 2911–2615 (1976). The activity of the holo-enzyme that can be obtained by the process according to the invention is thus ca. 0.5 to 3-fold higher than the activity that was achieved with acetyl CoA and apo-citrate lyase.

Hence the process according to the invention provides for the first time a recombinant protein with improved citrate lyase activity that is both soluble and active.

Furthermore the invention concerns a test kit for the determination of citric acid which is composed essentially of the following components: a protein obtainable by the process according to the invention with citrate lyase activity, at least one protein with hydrogen-transferring activity, nicotinamide-adenine dinucleotide or an appropriate derivative in a reduced form and optionally suitable stabilizers, activators and/or substances to avoid or reduce interferences i.e. components or reactions which mask or interfere with the actual reaction as well as suitable buffer solutions. In particular L-malate dehydrogenase and L-lactate dehydrogenase come into consideration as proteins with hydrogen-transferring activity. Those substances, additives or measures which help to avoid or at least to delay the degradation of a property or activity that is important for the determination are in principle suitable as stabilizers. Especially when only small amounts of sample material are available or if the samples are very dilute it can be advantageous to add activators.

An additional subject matter of the invention is the use of the recombinant soluble protein with citrate lyase activity to determine citric acid in clinical chemistry, food analysis and as a purity test for cosmetics. In clinical chemistry a corresponding enzymatic test is used primarily to examine fertility and for therapeutic monitoring of patients with kidney stones. In food analysis the most important application is analysis of wines and fruit juices.

The enzymatic method is based on the cleavage of citrate by the enzyme citrate lyase in the presence of $Mg^{2+}$ ions to form oxaloacetate and acetate. In the presence of hydrogen-transferring enzymes such as L-malate dehydrogenase and L-lactate dehydrogenase, oxaloacetate and its decarboxylation product pyruvate are reduced by reduced NADH or NADPH to form L-malate and L-lactate. The amount of NADH or NADPH is proportional to the amount of citrate and is measured at 334 nm, 340 nm or 365 nm.

Hence the invention also concerns a corresponding test kit for the determination of citric acid which, apart from suitable buffer solutions, contains a recombinant protein with citrate lyase activity, one or several hydrogen-transferring enzymes and a nicotinamide adenine dinucleotide or a corresponding derivative in a reduced form and optionally suitable stabilizers such as thiol reagents.

FIGURE LEGENDS

FIG. 1:

A: Function of the various subunits in a reaction catalysed by citrate lyase and activation of the enzyme by citrate lyase ligase. HS-R denotes a prosthetic group.

B. Structure of the prosthetic group of citrate lyase 2'-(5"-phosphoribosyl)-3'-phospho-CoA.

FIG. 2:

Citrate lyase gene cluster from *Klebsiella pneumoniae* (*K.p.*), *Escherichia coli* (*E.c.*) *Haemophilus influenzae* (*H.i.*) and *Leuconostoc mesenteroides* (*L.m.*). Gene sequences that are homologous to *E. coli* citX are shown by the light grey shading.

Figure 1:
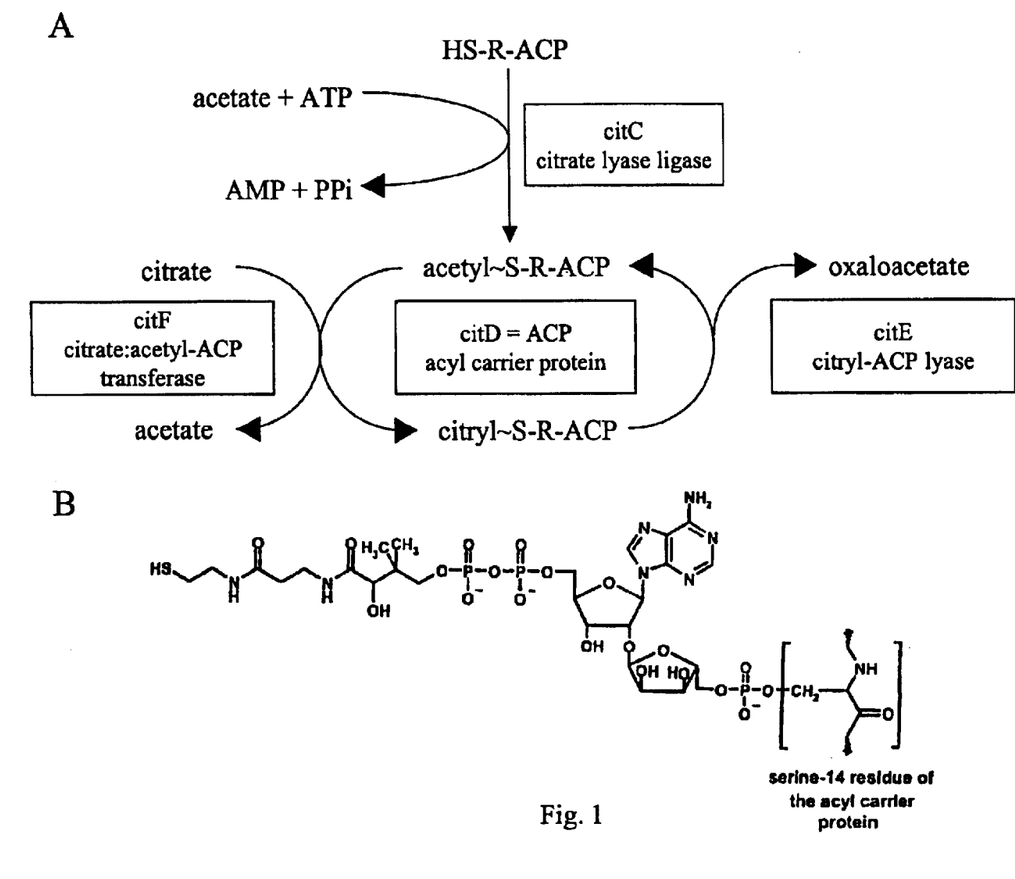
Figure 2:
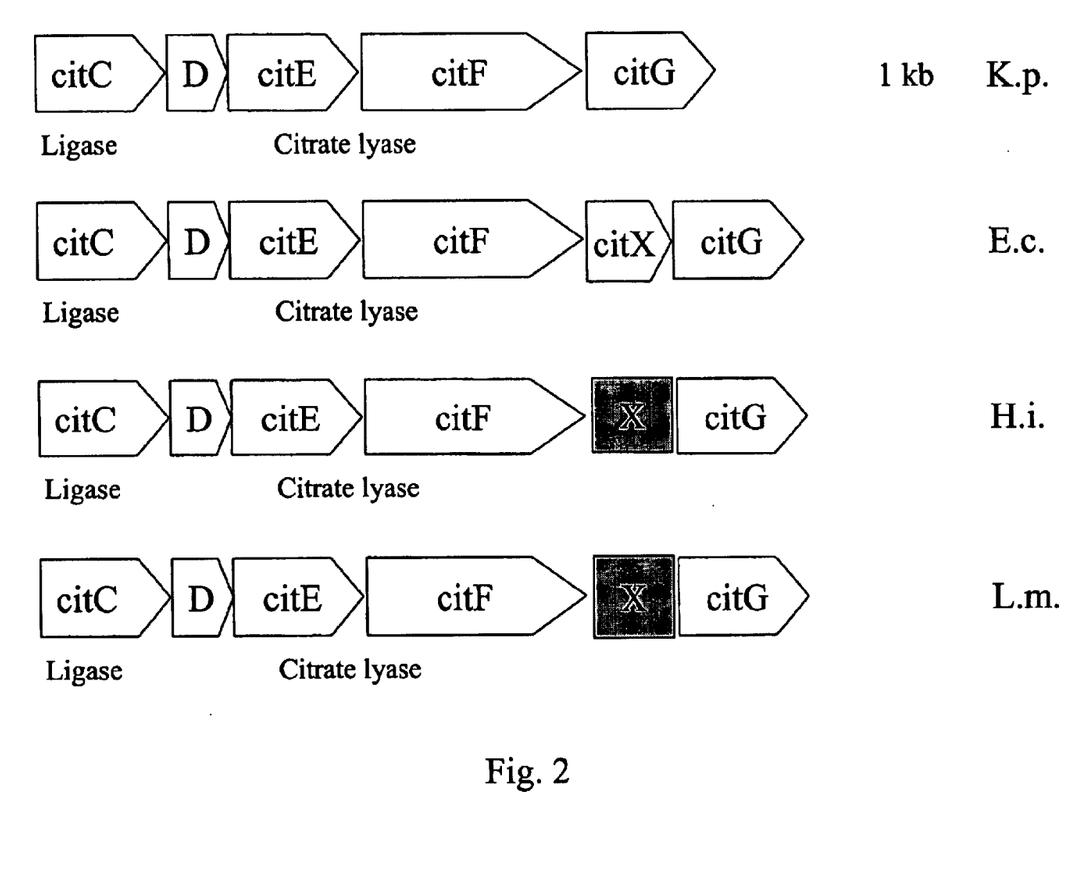

```
INFORMATION FOR SEQ ID NO. 1:
    SEQUENCE CHARACTERISTICS:
        (A) LENGTH: 36 base pairs
        (B) TYPE: nucleic acid
        (C) STRANDNESS: single
        (D) TOPOLOGY: linear

5'- CCCTCTAGAGAACAACATTCGTTGCAAATCGATAAC - 3'

INFORMATION FOR SEQ ID NO. 2:
    SEQUENCE CHARACTERISTICS:
        (A) LENGTH: 38 base pairs
        (B) TYPE: nucleic acid
        (C) STRANDNESS: single
        (D) TOPOLOGY: linear

5'- CCGCGAATTCTTAGTTCCACATGGCGAGAATCGGCCAG -3'

INFORMATION FOR SEQ ID NO. 3:
    SEQUENCE CHARACTERISTICS:
        (A) LENGTH: 5484 base pairs
        (B) TYPE: nucleic acid
        (C) STRANDNESS: single
        (D) TOPOLOGY: linear

1 GAACAACATT CGTTGCAAAT CGATAACAAC ATGCACCTTC AGGATACTAT
```

-continued

```
              ┌Start citC
  51 TTATTATGTT CGGCAATGAT ATTTTCACCC GCGTAAAACG TTCAGAAAAT
 101 AAAAAAATGG CGGAAATCGC CCAATTCCTG CATGAAAATG ATTTGAGCGT
 151 TGACACCACA GTCGAAGTAT TTATTACCGT AACCCGCGAT GAAAAGCTTA
 201 TCGCGTGCGG TGGAATTGCC GGAAATATTA TTAAATGCGT TGCTATCAGT
 251 GAATCCGTCC GCGGTGAAGG ACTGGCGCTG ACATTAGCCA CTGAATTGAT
 301 AAACCTCGCC TATGAGCGGC ACAGCACGCA TCTGTTTATT TATACCAAAA
 351 CCGAATACGA GGCGCTGTTC CGCCAGTGCG GTTTTTCCAC GCTGACCAGC
 401 GTACCCGGCG TGATGGTGCT GATGGAAAAC AGCGCCACGC GACTGAAACG
 451 CTATGCCGAA TCGCTGAAAA AATTTCGTCA TCCAGGGAAC AAGATTGGCT
 501 GCATTGTGAT GAACGCCAAT CCCTTTACGA ATGGTCACCG TTATCTGATT
 551 CAACAGGCTG CGGCACAGTG CGACTGGTTG CATCTGTTTT TAGTCAAAGA
 601 AGATTCTTCA CGCTTCCCCT ATGAAGACCG GCTGGATTTG GTGTTAAAAG
 651 GCACCGCCGA TATTCCACGC CTGACTGTGC ATCGTGGCTC CGAATACATC
 701 ATCTCCCGCG CTACGTTCCC TTGCTACTTC ATTAAAGAAC AGAGCGTCAT
 751 TAACCATTGT TACACCGAAA TTGATCTGAA GATTTTCCGT CAGTACCTCG
 801 CTCCCGCGCT GGGTGTAACT CACCGCTTTG TCGGTACTGA ACCCTTTTGT
 851 CGCGTTACCG CCCAGTACAA CCAGGATATG CGCTACTGGC TGGAAACGCC
 901 GACTATCTCC GCACCGCCCA TCGAACTGGT TGAAATTGAG CGGCTGCGTT 951 ACCAGGAGAT GCCGATATCC GCTTCCCGGG TACGTCAACT GCTGGCGAAA
1001 AACGATCTCA CGGCTATCGC GCCGCTGGTC CCTGCAGTCA CGCTGCATTA
1051 TTTGCAGAAC CTGCTTGAGC ACTCCCGCCA GGACGCGGCA GCTCGTCAAA Stop citC┐               ┌Start citD
1101 AGACCCCCGC ATGAGAAACA GGTGAAAAAT GAAAATAAAC CAGCCCGCCG
1151 TTGCAGGCAC CCTTGAGTCT GGGGATGTGA TGATACGCAT CGCCCCACTC
1201 GATACGCAGG ATATCGACCT GCAAATCAAT AGCAGCGTTG AGAAACAGTT
1251 TGGCGATGCA ATTCGCACCA CCATTCTGGA CGTTCTCGCC CGCTACAACG
1301 TGCGCGGCGT ACAGCTGAAT GTCGATGACA AAGGCGCACT GGACTGCATT
1351 TTACGTGCAC GACTGGAAGC CCTGCTGGCA CGCGCCAGCG GTATCCCGGC Stop citD┐
1401 TCTGCCATGG GAGGATTGCC AATGATTTCC GCTTCGCTGC AACAACGTAA
                       └Start citE 1451 AACTCGCACC CGCCGCAGCA TGTTGTTTGT GCCTGGTGCC AATGCCGCGA
1501 TGGTCAGCAA CTCCTTCATC TACCCGGCTG ATGCCCTGAT GTTTGACCTC
1551 GAAGACTCCG TAGCATTGCG TGAAAAAGAC ACCGCCCGCC GCATGGTTTA
1601 CCACGCGCTG CAACATCCGC TGTATCGCGA TATTGAAACC ATTGTGCGTG
1651 TCAACGCGCT GGATTCCGAA TGGGGTGTTA ACGACCTGGA AGCCGTCGTT
1701 CGCGGTGGTG CGGACGTTGT GCGTCTGCCG AAAACCGATA CCGCTCAGGA
1751 TGTTCTGGAT ATTGAAAAAG AGATCCTGCG TATCGAAAAA GCCTGTGGTC
1801 GTGAACCCGG CAGCACCGGC CTGCTGGCGG CGATTGAATC TCCGCTGGGG
1851 ATTACCCGCG CAGTGGAAAT CGCTCACGCT TCCGAGCGTT TGATCGGTAT
1901 CGCCCTCGGT GCAGAAGACT ATGTGCGCAA CCTGCGTACA GAACGCTCCC
1951 CGGAAGGAAC TGAACTGCTG TTCGCACGCT GTTCCATTTT GCAGGCCGCG
2001 CGCTCTGCGG GTATTCAGGC GTTCGATACC GTCTATTCCG ACGCTAACAA
2051 CGAAGCCGGA TTTCTGCAAG AAGCCGCCCA CATCAAACAG CTGGGCTTTG
2101 ACGGCAAATC GCTGATCAAC CCGCGTCAGA TTGATCTGCT GCACAACCTC
2151 TACGCACCGA CCCAGAAAGA AGTGGATCAC GCCCGCCGCG TCGTAGAAGC
2201 CGCTGAAGCC GCCGCTCGCG AAGGCCTCGG CGTGGTTTCC CTGAACGGCA
2251 AGATGGTGGA CGGTCCGGTT ATCGATCGCG CCCGTCTGGT GCTCTCCCGT Stop citE┐             ┌Start citF
2301 GCAGAACTTT CCGGCATCCG CGAAGAATAA GGCAATCAAA ATGACGCAGA
2351 AAATTGAACA ATCTCAACGA CAAGAACGGG TAGCGGCCTG GAATCGTCGC
2401 GCTGAATGCG ATCTTGCCGC TTTCCAGAAC TCGCCAAAGC AAACCTACCA
2451 GGCTGAAAAA GCGCGCGATC GCAAACTGTG CGCCAACCTG GAAGAAGCGA
2501 TTCGTCGCTC TGGTTTACAG GACGGCATGA CGGTTTCCTT CCATCACGCT
2551 TTCCGTGGCG GTGACCTGAC CGTCAATATG GTGATGGACG TCATCGCGAA
2601 GATGGGCTTT AAAAACCTGA CCCTGGCGTC CAGCTCCCTG AGTGATTGCC
2651 ATGCGCCGCT GGTAGAACAC ATTCGCCAGG GCGTGGTTAC CCGCATTTAT
2701 ACCTCCGGCC TGCGTGGTCC ACTGGCGGAA GAGATCTCCC GTGGTCTGCT
2751 GGCAGAACCG GTGCAGATCC ACTCTCACGG CGGTCGTGTG CATCTGGTAC
2801 AGAGCGGCGA ACTGAATATC GACGTGGCTT TCCTCGGCGT CCCGTCCTGT
2851 GATGAATTCG GTAATGCCAA CGGCTACACC GGTAAAGCCT GCTGCGGCTC
2901 CCTCGGCTAT GCAATAGTTG ATGCCGACAA CGCAAAACAG GTCGTGATGC
2951 TTACCGAAGA ACTGCTGCCT TATCCGCATA ATCCGGCAAG CATTGAGCAA
3001 GATCAGGTTG ATTTGATCGT CAAAGTTGAC CGCGTTGGCG ATGCTGCAAA
3051 AATCGGCGCT GGCGCGACCC GTATGACCAC TAACCCGCGC GAACTGCTTA
3101 TTGCCCGTAG CGCTGCGGAT GTGATTGTCA ACTCTGGCTA CTTCAAAGAA
3151 GGTTTCTCCA TGCAAACCGG CACCGGCGGC GCATCGCTGG CGGTAACCCG
3201 TTTCCTGGAA GACAAAATGC GTAGCCGCGA TATTCGCGCC GACTTCGCCC
3251 TTGGCGGTAT TACCGCGACG ATGGTTGACC TGCACGAAAA AGGTCTGATC
3301 CGCAAACTGC TGGATGTGCA GAGCTTTGAC AGCCATGCTG CGCAATCGCT
3351 GGCCCGTAAC CCCAATCACA TCGAAATCAG CGCCAACCAG TACGCTAACT 3401 GGGGTTCGAA AGGCGCATCG GTTGATCGTC TCGACGTGGT GGTACTGAGC
3451 GCGCTGGAAA TTGACACCCA GTTCAACGTT AACGTGCTGA CCGGCTCTGA
3501 CGGCGTACTG CGTGGTCGTT CCGGTGGTCA CTGCGATACC GCGATTGCCT
3551 CTGCGCTTTC CATCATCGTC GCGCCGCTGG TACGCGGTCG TATTCCGACT
3601 CTGGTGGATA ACGTACTGAC CTGCATCACC CCAGGCTCCA GTGTCGATAT
3651 TCTGGTCACA GACCACGGTA TCGCAGTTAA CCCGGCACGT CCGGAACTGG
3701 CAGAACGTCT GCAGGAAGCG GGCATTAAAG TGGTTTCCAT TGAGTGGCTG
3751 CGCGAACGTG CGCGTCTGCT GACCGGTGAA CCACAGCCGA TTGAATTCAC
3801 AGACCGCGTC GTTGCCGTTG TGCGTTACCG CGATGGCTCG GTGATCGATG
```

```
                  Stop citF┐    ┌Start citX
3851 TTGTGCATCA GGTGAAGGAA TAAGCCATGC ACCTGCTTCC TGAACTCGCC
3901 AGCCACCATG CGGTATCAAT TCCCGAGCTG CTCGTCAGCC GGGATGAAAG
3951 GCAAGCACGG CAACACGTCT GGCTCAAGCG CCATCCTGTT CCACTGGTCT
4001 CCTTTACCGT GGTTGCGCCT GGGCCGATTA AAGACAGCGA GGTCACACGC
4051 CGAATTTTTA ATCATGGCGT GACAGCCTTG CGTGCCTTAG CCGCAAAACA
4101 GGGCTGGCAA ATTCAGGAGC AGGCTGCACT GGTTTCCGCC AGCGGGCCGG
4151 AGGGCATGTT GAGCATTGCC GCCCCGGCTC GCGACCTCAA GCTCGCCACC
4201 ATTGAGCTTG AACATAGTCA TCCTCTCGGG CGGTTATGGG ATATCGATGT
4251 CCTGACGCCC GAAGGCGAAA TTCTCTCCCG CCGCGACTAT TCACTGCCGC
4301 CTCGCCGCTG CCTGTTGTGC GAACAAAGCG CAGCCGTCTG CGCGCGTGGA
4351 AAAACCCATC AACTGACCGA TTTACTCAAC CGCATGGAGG CACTGCTGAA Stop citX┐
4401 CGATGTCGAT GCCTGCAACG TCAACTAAAA CCACAAAGCT TGCGACGTCA
         └Start citG 4451 TTAATCGATG AGTACGCCCT GCTGGGCTGG CGCGCCATGC TGACTGAAGT
4501 CAATCTGTCA CCGAAACCAG GCCTCGTGGA TCGCATTAAC TGCGGTGCGC
4551 ACAAAGATAT GGCGCTGGAA GATTTCCACC GCAGCGCGCT GGCGATTCAG
4601 GGCTGGCTAC CCCGTTTCAT TGAATTTGGT GCCTGTAGTG CGGAAATGGC
4651 ACCAGAAGCG GTACTCCACG GATTACGCCC AATTGGTATG GCTTGCGAAG
4701 GTGATATGTT CCGCGCCACT GCGGGCGTAA ACACGCATAA AGGCAGCATT
4751 TTTTCTTTAG GGCTGCTATG TGCGGCAATT GGCCGTTTGC TTCAACTCAA
4801 CCAACCGGTA ACGCCAACAA CCGTTTGTTC TACGGCGGCA AGTTTCTGCC
4851 GTGGCCTGAC CGATCGCGAA CTGCGTACCA ATAATTCACA ACTGACGGCA
4901 GGTCAACGGT TGTACCAACA GCTTGGCCTT ACCGGCGCAC GCGGTGAAGC
4951 CGAAGCGGGT TATCCACTGG TGATCAATCA CGCCTTGCCG CATTACCTCA
5001 CTCTGCTGGA TCAGGGGTTA GATCCTGAAC TGGCATTGCT CGATACCTTG
5051 CTCCTACTGA TGGCGATCAA CGGCGATACC AACGTTGCAT CGCGCGGTGG
5101 CGAGGGGGGC CTGCGCTGGC TACAGCGCGA GGCGCAAACA TTATTGCAAA
5151 AAGGGGGCAT TCGAACCCCC GCCGATCTCG ATTATCTCCG GCAGTTCGAC
5201 AGGGAGTGTA TCGAACGAAA TCTCAGTCCA GGCGGCAGTG CTGACCTACT Stop citG┐
5251 GATCCTTACC TGGTTTTTAG CACAGATTTA ATTATTTAAG CACTTGATAA ┌Start citT
5301 ATTTGGAAAT ATTAATTTTC GGAGAACCCG TATGTCTTTA GCAAAAGATA
5351 ATATATGGAA ACTATTGGCC CCACTGGTGG TGATGGGTGT CATGTTTCTT
5401 ATCCCTGTCC CCGACGGTAT GCCGCCGCAG GCATGGCATT ACTTCGCTGT
5451 GTTTGTGGCA ATGATTGTCG GCATGATCCT CGAG INFORMATION FOR SEQ ID NO. 4:
    SEQUENCE CHARACTERISTICS:
        (A) LENGTH: 33 base pairs
        (B) TYPE: nucleic acid
        (C) STRANDNESS: single
        (D) TOPOLOGY: linear

5'- AAATTTCATATGCACCTGCTTCCTGAACTCGCC - 3'

INFORMATION FOR SEQ ID NO. 5:
    SEQUENCE CHARACTERISTICS:
        (A) LENGTH: 36 base pairs
        (B) TYPE: nucleic acid
        (C) STRANDNESS: single
        (D) TOPOLOGY: linear

5'- GGGCCCCTCGAGTTAGTTGACGTTGCAGGCATCGAC - 3'

INFORMATION FOR SEQ ID NO. 6:
    SEQUENCE CHARACTERISTICS:
        (A) LENGTH: 553 base pairs
        (B) TYPE: nucleic acid
        (C) STRANDNESS: single
        (D) TOPOLOGY: linear 1 ATGCACCTGC TTCCTGAACT CGCCAGCCAC CATGCGGTAT CAATTCCCGA
 51 GCTGCTCGTC AGCCGGGATG AAAGGCAAGC ACGGCAACAC GTCTGGCTCA
101 AGCGCCATCC TGTTCCACTG GTCTCCTTTA CCGTGGTTGC GCCTGGGCCG
151 ATTAAAGACA GCGAGGTCAC ACGCCGAATT TTTAATCATG GCGTGACAGC
201 CTTGCGTGCC TTAGCCGCAA AACAGGGCTG GCAAATTCAG GAGCAGGCTG
251 CACTGGTTTC CGCCAGCGGG CCGGAGGGCA TGTTGAGCAT TGCCGCCCCG
301 GCTCGCGACC TCAAGCTCGC CACCATTGAG CTTGAACATA GTCATCCTCT
351 CGGGCGGTTA TGGGATATCG ATGTCCTGAC GCCCGAAGGC GAAATTCTCT
401 CCCGCCGCGA CTATTCACTG CCGCCTCGCC GCTGCCTGTT GTGCGAACAA
451 AGCCAGCCG TCTGCGCGCG TGGAAAAACC CATCAACTGA CCGATTTACT
501 CAACCGCATG GAGGCACTGC TGAACGATGT CGATGCCTGC AACGTCAACT
551 AA INFORMATION FOR SEQ ID NO. 7:
    SEQUENCE CHARACTERISTICS:
        (A) LENGTH: 5593 base pairs
        (B) TYPE: nucleic acid
        (C) STRANDNESS: single
        (D) TOPOLOGY: linear 1 TTAATTAACA ACATAAAAAC CATAAAGCCA ATTAAGCCAC GAGAAAAACT GTGACTTAAA
 61 TACAAGAATC CATAGCCGAA CGCTGGCGAA ATACAGTTCG TTTTGAAATG ACGAAGCGCT
```

-continued

```
              ┌Start citCe
 121 AAAAAATGAC ACTGATATTA AAACGCGTTC AGCTATTAAA AGATAAACCG CGGCGAGAGG
 181 CGATCGATCG GTTTCTCCGC CAGCATCAAC TGTCGTTAGA GGCCGACTGC GAAATGGCGA
 241 TTATCGCCGA GTATCAGCAG CGGCTGGTCG GCTGCGGTGC TATCGCCGGC AATGTGCTGA
 301 AATGCATCGC CATCGATCCC TCGCTGCAGG GGGAGGGGCT GAGCCTTAAA TTACTGACCG
 361 AGCTCCTGAC GCTGGCCTAT GAGCTGGGGC GCAGCGAACT GTTTTTGTTC ACTAAACCTT
 421 GCAATGCCGC GTTATTTTCC GGCGCCGGCT TCTGGCCGAT AGCCCAGGCG GGCGACCGCG
 481 CCGTGCTAAT GGAAAATAGC CGCGAACGGC TGACTCGTTA CTGTCGACAG CTGGCGATGT
 541 ACCGTCAGCC GGGAAGAAAA ATCGGCGCTA TCGTGATGAA TGCTAATCCA TTCACCCTCG
 601 GCCACCGCTG GTTGGTAGAA CAGGCGGCCA GCCAGTGCGA CTGGCTGCAT CTGTTTGTGG
 661 TCAAAGAAGA TGCGTCCTGC TTTTCCTATC ACGATCGCTT CAAGCTCATT GAACAGGGGA
 721 TTACCGGCAT CGATAAGGTG ACGCTGCATC CCGGTTCGGC GTATCTGATC TCGCGGGCGA
 781 CGTTCCCCGG CTATTTCCTG AAAGAGCAGG GGGTGGTTGA TGACTGCCAC AGCCAGATTG
 841 ACCTGCAGCT CTTCCGCGAG CGCCTGGCCC CGGCGCTGCA GATTACCCAT CGCTTTGTCG
 901 GCACCGAGCC GCTGTGTCCC CTGACCCGTA ATTACAACCA GCGCATGAAG TCACTACTGG
 961 AAGCGCCAGG CGACGCGCCG CCCATTGAAG TAGTTGAGCT TGCGCGAATC GAAAAAAATG
1021 GTGGACCCGT GTCGGCCTCC CGAGTGCGCG AACTCTATCG ACAGCGCAAC TGGCAGGCGG
1081 TCGCGGCGCT GGTACCGCCG GGAACCCTCT CTTTTCTGAT GCAACTGGCG GAAAGCGAAC
     Stop citC┐                          ┌Start citD
1141 ATCAAACCGC CTGATTTATA CGCCCTAACT AAGGATTTTC CCCTATGGAA ATGAAGATTG
1201 ACGCCCTGGC CGGCACGCTG GAGTCCAGCG ATGTGATGGT CAGGATTGGA CCCGCGGCGC
1261 AGCCGGGCAT TCAGCTGGAA ATCGACAGCA TTGTGAAACA ACAGTTTGGC GCTGCGATTG
1321 AGCAGGTAGT GAGAGAAACG CTGGCTCAGC TTGGCGTGAA ACAGGCCAAC GTGGTGGTCG
1381 ATGATAAAGG CGCGCTGGAA TGTGTTTTGC GAGCTCGCGT ACAGGCCGCG GCGCTGCGCG
                              Stop citD┐
1441 CGGCGCAACA GACCCAATTA CAATGGAGCC AGCTATGAAA CCACGTCGCA GTATGTTGTT
                                       └Start citE
1501 CATCCCTGGC GCCAATGCCG CCATGTTAAG CACGTCATTC GTCTACGGCG CTGATGCTGT
1561 GATGTTCGAC CTGGAAGATG CCGTTTCGCT GCGCGAAGAA GATACCGCTC GTCTGCTGGT
1621 GTATCAGGCG CTGCAGCATC CACTGTATCA GGATATCGAA ACCGTGGTGC GTATTAACCC
1681 GCTAAATACC CCGTTTGGTC TGGCCGATCT GGAAGCCGTG GTTCGTGCGG GCGTGGATAT
1741 GGTGCGTCTG CCGAAAACCG ACAGCAAAGA AGATATCCAT GAGCTGGAAG CGCATGTTGA
1801 GCGGATTGAA CGCGAGTGCG GCCGGGAAGT GGGGCAGCAC CAAGTTAATG CGGCGATCGA
1861 GTCGGCGCTG GGCGTGGTGA ACGCGGTGGA AATCGCCCGC GCCAGCCCGC GTCTGGCGGC
1921 GATCGCGCTG GCGGCCTTCG ATTACGTGAT GGATATGGGC ACCTCCCGCG GCGACGGTAC
1981 TGAACTGTTC TACGCCCGCT GCGCTGTACT GCATGCCGCC CGCGTTGCCG GCATCGCCGC
2041 CTATGACGTG GTGTGGTCGG ATATCAATAA TGAAGAGGGC TTCCTGGCGG AAGCGAATCT
2101 GGCCAAAAAC CTCGGCTTTA ACGGCAAATC GTTGGTTAAC CACGACAAA TTGAACTCCT
2161 GCATCAGGTC TATGCCCCGA CGCGCAAAGA GGTCGATCAC GCGCTGGAAG TGATTGCCGC
2221 GGCGGAAGAA GCCGAAACGC GAGGTCTGGG TGTGGTATCG CTGAACGGCA AGATGATCGA
2281 TGGACCGATT ATCGACCATG CTCGCAAAGT GGTGGCGCTC TCGGCTTCCG GTATTCGTGA
     Stop┬citE         ┌Start citF
2341 TTAAGGGGAA TAAGATGAAA GAGACAGTAG CAATGCTTAA TCAGCAGTAC GTGATGCCGA
2401 ATGGACTGAC ACCTTATGCC GGCGTAACGG CGAAAAGTCC CTGGCTGGCG AGTGAGAGCG
2461 AAAAGCGCCA GCGCAAAATC TGCGATTCGC TGGAAACGGC AATCCGTCGC TCCGGCCTGC
2521 AAAACGGCAT GACCATCTCG TTTCACCACG CGTTTCGCGG CGGTGACAAA GTCGTCAATA
2581 TGGTAGTGGC GAAGCTGGCG GAAATGGGTT TTCGCGATCT CACCCTGGCG TCCAGTTCGC
2641 TGATCGACGC CCACTGGCCG CTGATCGAGC ATATTAAAAA TGGCGTGATC CGCCAGATCT
2701 ACACCTCCGG CCTGCGCGGC AAGTTGGGCG AGGAGATCTC CGCCGGTTTA ATGGAAAACC
2761 CGGTGCAGAT CCACTCCCAC GGCGGTCGCG TACAGCTGAT TCAAAGCGGC GAGCTGTCGA
2821 TTGATGTCGC GTTTCTCGGC GTTCCTTGCT GCGATGAGTT TGGCAACGCC AACGGCTTTA
2881 GCGGTAAATC ACGCTGCGGT TCTCTGGGCT ACGCGCCGAG CGATGCCGAG CACGCTAAAT
2941 GCGTGGTGCT GCTCACCGAA GAGTGGGTGG ATTATCCTAA CTATCCGGCC AGTATTGCCC
3001 AGGATCAGGT GGATCTGATA GTCCAGGTAG ATGAAGTCGG CGATCCGCAA AAAATTACCG
3061 CGGGTGCCAT CCGTCTGACC AGCAACCCGC GCGAGCTGCT GATCGCCCGC CAGGCGGCGA
3121 AAGTCGTTGA GCACTCCGGT TACTTTAAAG AGGGTTTCTC GCTGCAGACC GGTACCGGCG
3181 GCGCCTCGCT GGCAGTAACT CGCTTCCTTG AAGATAAAAT GCGCCGTAAC GGCATTACCG
3241 CCAGCTTCGG CCTCGGCGGT ATCACCGGGA CGATGGTCGA TTTGCACGAA AAAGGGTTGA
3301 TCAAAACGCT GCTCGATACC CAGTCCTTCG ATGGTGACGC GGCGCGTTCG CTGGCGCAGA
3361 ACCCGAACCA TGTCGAGATC TCCACCAATC AGTATGCCAG CCCGGGCTCC AAAGGCGCCT
3421 CCTGCGAGCG CTTAAACGTG GTGATGCTCA GCGCGCTGGA AATTGATATC GACTTTAACG
3481 TTAACGTGAT GACCGGTTCT AACGGTGTGC TGCGCGGGGC GTCCGGTGGC CATAGCGATA
3541 CCGCCGCCGG TGCGGATTTG ACCATTATTA CCGCGCCGTT AGTTCGCGGC CGTATTCCCT
3601 GCGTCGTGGA AAAGGTGCTG ACCCGCGTCA CGCCGGGGGC CAGCGTGGAT GTGCTGGTCA
3661 CTGACCACGG CATTGCGGTC AACCCGGCAC GTCAGGACCT GATCGACAAT TTGCGCAGCG
3721 CAGGCATTCC GCTGATGACC ATTGAGGAAC TGCAGCAGCG TGCTGAGCTG TTGACTGGCA
3781 AGCCGCAGCC GATCGAATTC ACCGATCGGG TGGTGGCGGT GGTGCGCTAT CGCGACGGTT
                                                    Stop          citF┘
     ┌Start
3841 CGGTCATCGA TGTGATTCGT CAGGTGAAAA ACAGCGACTA AACGCAGAGG GGAAAGGCCA
     citG
3901 TGAGCGACGT GTTAATTAAT CCTGCGCGTG TGCGGCGCGT GAAGCCACTG AGTGCCGAAG
3961 AGGTGGTCAG CGCGGTAGAG GCGCGCTGT TGACCGAAGT TCGCCTGACC CCAAAGCCCG
4021 GGTTGGTGGA TATTCGTAAC GCTGGCGCGC ACTGGGATAT GGATCTGGCC TCGTTTGAGG
4081 CCAGCACCGC GGTGGTGGCT CCGTGGATGG AGAAATTTTT CATCATGGGC CACGATACTG
4141 CGGCGGTCGC GCCGGAGCAG GTATTGATGA TGCTGCGCCC GGTAGGGATG GCCTGTGAGA
4201 ACGATATGCT GGAGGCCACC GGCGGGGTGA ATACCCATCG CGGGGCGATC TTCGCTTTTG
4261 GCCTGCTCAG CGCGGCGGCG GGCAGGCTGG TGTCGAAAGG TGAGCCGATA GAGCAGCACC
4321 GGCTTTGCGA CCAGGTGGCG CGCTTCTGTC GCGGCATGGT TATGCAGGAG TTGTCTTCTG
4381 CTGGCGGGGA ACGGCTCAGT AAAGGCGAGG CTCATTTTCT ACGCTATGGT CTCTCCGGGG
4441 CCCGCGCGCA GGCGGAGAGC GGTTTCCTGA CGGTGCGTAC CCAGGCCATG CCAGTCTTTA
4501 CCCGCATGAT GGAAGAGACC GGCGACAGTA ATCTGCGCT ACTGCAAACC CTGCTGCATC
4561 TGATGGCGTG GAATGATGAC ACCAACCTGG TCTCGCGCGG CGGGCTTGCC GGGCTGAACT
4621 TTGTCCAGCA GGAGGCGCAG CGACTGCTGT GGCAGGGCGG CGTGCTGCCG GACGGCGGGC
4681 TGGAGGCGCT GCGACAGTTT GACGATGAGC TGATTGCCCG CCATCTCAGC CCTGGCGGCA
4741 GCGCCGATCT GTTGGCGGTG ACCTGGTTTT TATCCGCGTT TCCCGCCGGC GCGCTTTTCC
```

-continued

```
Stop citG
4801 CGCTGTAACC CACTGCAATA CCGCCTTCGC CCGCACTGTA CGGGCGAGGG CGCCATCATT
4861 AGCCTTCCCG GTTGTCATCC GGTAAACACG GAATCGCGGC ACAATCGTAT AGTTTTTACT
4921 GATATCGTCC GCCGTTTGTC ATAAATTTCT AATTATCGGC GTTTTTGAGT AGCGGCCCGC
4981 TGACGGGCTG GTTACTCTGA AAACAATTTA CGTAATGTTA ACAAAAGAGA ATAGCTATGC
5041 ATGATGCACA AATCCGCGTG GCCATCGCCG GCGCGGGCGG CCGGATGGGA CGCCAGTTAA
5101 TTCAGGCTGC ATTGCAGATG GAAGGCGTGG CGCTGGGCGC GGCGCTGGAG CGCGAAGGGT
5161 CAAGCCTGGT GGGCAGCGAC GCCGGCGAGC TGGCGGGCGC CGGCAAAGCG GGCGTCGCGG
5221 TGCAGAGCAG CCTGGCGGCG GTAAAAGATG ATTTCGACGT GTTGATCGAT TTTACCCGCC
5281 CGGAAGGCAC GCTGAACCAT CTGGCGTTTT GCCGCGAGCA CGGCAAAGGG ATGGTCATCG
5341 GCACCACCGG TTTTGACGAC GCTGGCAAAC AGGCGATTCG CGATGCCGCG CAGGACATTG
5401 CCATTGTCTT CGCCGCTAAC TTTAGCGTTG GCGTCAATGT CCTGTTGAAG CTGCTGGAGA
5461 AGGCGGCGAA GGTGATGGGC GACTATACCG ACATCGAAAT TATCGAAGCG CACCACCGGC
5521 ATAAAGTGGA TGCGCCGTCA GGCACCGCGC TGGCGATGGG CGAAGCGATC GCCGGGGCAT
5581 TGAACAAAGA TCT
```

The invention is further elucidated by the following examples:

EXAMPLE 1

Cell Culture

The following strains and plasmids were used: E. coli DH5α or BL21 (DE3) (F. W. Studiar and B. A. Mofatt, J. Mol. Biol. Vol. 189, 113–130 (1986)) and pACYC184 (A. C. Y. Chang et al., J. Bacteriol. Vol. 134, 1141–1156 (1978)). The E. coli cells were routinely cultured in Luria Bertani (LB) medium at 37° C. according to J. Sambrook et al., Molecular Cloning. A Laboratory Manual, Cold Spring Harbor Laboratory Press, Cold Spring Harbor, N.Y. (2nd Edition 1989). Antibiotics were added at the following final concentrations: 200 µg/ml ampicillin, 50 µg/ml chloroamphenicol and 50 µg/ml kanamycin. The E. coli strain DH5α was used as the host organism for the cloning. The E. coli BL21 (DE3) cells which contain the phage T7 polymerase gene under the control of a lacUV5 promoter (F. W. Studier and B. A. Moffatt, supra) served as a host for the expression of the target genes of pT7-7 and pET derivatives. The cultures for the expression were prepared as follows. After centrifugation (3000 g, 8 min) of a preculture of 40 ml which had been incubated overnight at 37° C., the cells were resuspended in 20 ml fresh LB medium. The cell suspension was subsequently used to inoculate 2 L of the same medium which contained appropriate antibiotics and the culture was incubated at 37° C. in a shaker (180 rpm). When the $OD_{600}$ reached a value between 0.5 and 0.8, the expression of the target genes was induced by adding IPTG (isopropyl-β-D-thiogalactoside) at a final concentration of 1 mM and the culture was incubated for a further 3 hours at 37° C. in a shaker (180 rpm). Subsequently the cells were harvested by centrifugation (30 min at 3000 g), washed once with 20 ml 50 mM potassium phosphate, pH 7.0, 1 MM $MgCl_2$ and stored at −20° C.

EXAMPLE 2

Isolation of the Genes and Gene Cluster

For the construction of the expression plasmid which contains the E. coli citCDEFXG gene cluster, a 6.9 kb fragment from the chromosomal DNA of E. coli was amplified by means of PCR with the primers eccl-for (SEQ ID NO.1) and ec-citT-rev (SEQ ID NO.2) using the Expand High Fidelity PCR System from Roche Diagnostics. The 6.9 kb PCR fragment which additionally contains the citT gene (K. M. Pos et al., J. Bacteriol. Vol. 180, 4160–4165 (1998)), was cleaved with the restriction endonucleases XbaI and XhoI and the resulting 5.5 kb fragment (SEQ ID NO.3) and an expression vector that was also linearized correspondingly such as pKK177-3Hb, pKKT5, pUC18, pT7, pET24b were separated on an agarose gel and the appropriate bands were isolated (QIAEX kit from the Diagen Company). Subsequently the PCR fragment and the vector fragment were ligated together using T4 DNA ligase. For this 1 µl (20 ng) vector fragment and 3 µl (100 ng) PCR fragment, 1 µl 10× ligase buffer (Maniatis et al., 1989 B.27), 1 µl T4 DNA ligase, 4 µl sterile redistilled $H_2O$ were pipetted, carefully mixed and incubated overnight at 16° C. The insert obtained from the PCR starts 55 bp before the citC start codon and ends 203 bp downstream of the citG stop codon.

For the construction of the expression plasmid which contains the citX gene from E. coli (SEQ ID NO.3), the citX gene was amplified by PCR from the chromosomal DNA with the primers ec-citX-for (SEQ ID NO.4) and ec-citX-rev (SEQ ID NO.5) using the Pfu DNA polymerase (Stratagene). The start codon is part of an NdeI restriction endonuclease cleavage site and a XhoI restriction endonuclease cleavage site is located directly behind the stop codon. After digestion of the PCR product with NdeI and XhoI, the resulting 555 bp DNA fragment (SEQ ID NO.6) was ligated into appropriately linearized expression vectors (as described above).

The construction of the expression plasmid which contains the citCDEFG gene cluster of Klebsiella pneumoniae is described in M. Bott and P. Dimroth, Molecular Microbiology Vol. 14 (2), 347–356 (1994). The sequence of the citCDEFG gene cluster is shown in SEQ ID NO.7.

EXAMPLE 3

Transformation of the Various Expression Plasmids in Various E. coli Expression Strains Competent cells of various E. coli strains were prepared according to the method of Hanahan (J. Mol. Biol. Vol. 166, 557 ff. (1983)). 200 µl of cells prepared in this manner were mixed with 20 ng of the corresponding expression plasmids. After 30 minutes incubation on ice, a heat shock was carried out (90 sec. at 42° C.).

Subsequently the cells were transferred to 1 ml LB medium and incubated for 1 hour at 37° C. for the phenotypic expression. Aliquots of this transformation mixture were plated on LB plates containing the appropriate antibiotic as a selection marker and incubated for 15 hours at 37° C.

EXAMPLE 4

Expression of the Various Target Genes

After centrifugation (3000 g, 8 min) of 40 ml preculture which had been grown overnight at 37° C., the cell pellet was resuspended in 20 ml fresh LB medium. The cell suspension was then used to inoculate 2 l LB medium containing the appropriate antibiotics. This cell culture was incubated at 37° C. in a shaker (180 rpm). The expression of the target genes was induced at an optical density (measured at 600 nm) of 0.5–0.8 by adding 1 mM isopropyl-β-D-thiogalactoside (IPTG, final concentration) and the cultures were incubated for a further 3 hours at 37° C. and 180 rpm. Afterwards the cells were harvested by centrifugation (30 min. at 3000 g), washed once in 20 ml 50 mM potassium phosphate, pH 7.0 and frozen at −20° C.

For the cell extract preparation, 1 g cells (wet weight) were resuspended in 4 ml cold 50 mM potassium phosphate, 1 mM $MgCl_2$ pH 7.0. After adding a protease inhibitor cocktail (Roche Diagnostics) and DNAseI to a final concentration of 25 mg/ml, the cells were lysed by a three-fold passage in a French press at 108 Mpa. Intact cells and cell debris were removed by centrifugation (30 min. at 27,000 g). The cell-free supernatant was separated from the membrane fraction by ultracentrifugation (1 H at 150,000 g) and the resulting cell extract can then be used directly for enzymatic studies and for protein purification.

EXAMPLE 5

Citrate Lyase Activity Test

The citrate lyase activity was measured at 25° C. in a spectrophotometric test coupled with malate dehydrogenase from Roche Diagnostics. The test mixture contained in a final volume of 1 ml 50 mM glycylglycine pH 7.9, 5 mM potassium citrate, 2 mM $ZnCl_2$, 0.5 mM NADH, 30 U malate dehydrogenase (Roche Diagnostics) and 10 μl or 20 μl cell extract. The oxidation of NADH was measured in a spectrophotometer at 365 nm ($\epsilon$=3.4 $mM^{-1}$ $cm^{-1}$). One enzyme unit (unit) is defined as 1 μmol citrate which is degraded per minute to acetate and oxaloacetate.

What is claimed is:

1. A method for the production of a protein with citrate lyase activity, said method comprising the steps of expressing a suitable plasmid in a host organism and isolating the protein in an active form, wherein the host organism is *E. coli* and wherein the plasmid comprises an inducible promoter and a gene cluster comprising the genes citC, citD, citE, citF, and citG in that order from *Klebsiella pneumoniae* and citX from *E. coli*.

2. The method of claim 1, wherein the genes code for certain subunits of the protein having citrate lyase activity and for components that contribute to the biosynthesis of the complete enzyme.

3. The method of claim 1, wherein one of the genes codes for a 20 kDa protein.

4. The method of claim 1, wherein one of the genes codes for a protein containing the motif $X_1$—R—L—$X_2$—D—$X_3$—D—V, wherein $X_1$ is optionally G or A, $X_2$ is any amino acid, and $X_3$ is optionally L or I.

5. The method of claim 1, wherein the expression occurs under aerobic conditions.

* * * * *